US011383247B2

(12) United States Patent
Koser (10) Patent No.: US 11,383,247 B2
(45) Date of Patent: Jul. 12, 2022

(54) SYSTEMS AND METHODS FOR ACTIVE PARTICLE SEPARATION

(71) Applicant: Ancera, LLC, Branford, CT (US)

(72) Inventor: Hur Koser, Wallingford, CT (US)

(73) Assignee: ANCERA, LLC, Branford, CT (US)

( * ) Notice: Subject to any disclaimer, the term of this patent is extended or adjusted under 35 U.S.C. 154(b) by 96 days.

(21) Appl. No.: 16/013,793

(22) Filed: Jun. 20, 2018

(65) Prior Publication Data

US 2019/0118190 A1  Apr. 25, 2019

Related U.S. Application Data

(63) Continuation of application No. 14/777,505, filed as application No. PCT/US2014/029336 on Mar. 14, 2014, now abandoned.

(60) Provisional application No. 61/794,885, filed on Mar. 15, 2013.

(51) Int. Cl.
| | |
|---|---|
| *B03C 1/32* | (2006.01) |
| *C02F 1/44* | (2006.01) |
| *C02F 1/48* | (2006.01) |
| *B03C 1/28* | (2006.01) |
| *B03C 1/023* | (2006.01) |
| *B03C 1/033* | (2006.01) |
| *B03C 1/253* | (2006.01) |
| *C12N 13/00* | (2006.01) |
| *G01N 35/00* | (2006.01) |

(52) U.S. Cl.
CPC .............. *B03C 1/32* (2013.01); *B03C 1/023* (2013.01); *B03C 1/0332* (2013.01); *B03C 1/0335* (2013.01); *B03C 1/253* (2013.01); *B03C 1/288* (2013.01); *C02F 1/44* (2013.01); *C02F 1/488* (2013.01); *C12N 13/00* (2013.01); *B03C 2201/18* (2013.01); *B03C 2201/26* (2013.01); *G01N 35/0098* (2013.01)

(58) Field of Classification Search
CPC ......... B03C 1/32; B03C 1/023; B03C 1/0332; B03C 1/0335; B03C 1/253; B03C 1/288; B03C 2201/26; B03C 2201/18; C12N 13/00; C02F 1/44; C02F 1/488; G01N 35/0098

See application file for complete search history.

(56) References Cited

U.S. PATENT DOCUMENTS

| | | | |
|---|---|---|---|
| 3,764,540 A | 10/1973 | Khalafalla et al. | |
| 3,898,156 A * | 8/1975 | Kaiser | B03C 1/32 209/1 |
| 4,448,534 A | 5/1984 | Wertz et al. | |
| 4,935,147 A | 6/1990 | Ullman et al. | |
| 5,076,950 A | 12/1991 | Ullman et al. | |
| 5,194,133 A | 3/1993 | Clark et al. | |
| 5,439,586 A | 8/1995 | Richards et al. | |
| 5,932,100 A | 8/1999 | Yager et al. | |
| 5,998,224 A | 12/1999 | Rohr et al. | |
| 6,038,104 A | 3/2000 | Sato et al. | |
| 6,432,630 B1 | 8/2002 | Blankenstein | |
| 6,596,143 B1 | 7/2003 | Wang et al. | |
| 6,610,186 B1 | 8/2003 | Mayer et al. | |
| 6,620,627 B1 | 9/2003 | Liberti et al. | |
| 6,663,757 B1 | 12/2003 | Fuhr et al. | |
| 7,960,311 B2 | 6/2011 | Carlson | |
| 8,364,409 B2 | 1/2013 | Rieder et al. | |
| 8,961,878 B2 | 2/2015 | Koser | |
| 8,961,898 B2 | 2/2015 | Nisisako et al. | |
| 9,352,317 B2 | 5/2016 | Koser | |
| 9,415,398 B2 | 8/2016 | Yellen et al. | |
| 9,726,592 B2 | 8/2017 | Koser | |
| 9,999,855 B2 | 6/2018 | Koser | |
| 10,302,634 B2 | 5/2019 | Koser | |
| 10,632,463 B2 | 4/2020 | Koser | |
| 10,782,223 B2 | 9/2020 | Koser | |
| 11,204,350 B2 | 12/2021 | Koser | |
| 2002/0003001 A1 | 1/2002 | Weigl et al. | |
| 2002/0016751 A1 | 2/2002 | Sekiya | |
| 2002/0049782 A1 | 4/2002 | Herzenberg et al. | |
| 2002/0059132 A1 | 5/2002 | Quay et al. | |
| 2002/0106314 A1 | 8/2002 | Pelrine et al. | |
| 2002/0144934 A1 | 10/2002 | Exner | |
| 2003/0159999 A1 | 8/2003 | Oakey et al. | |
| 2003/0203507 A1 | 10/2003 | Liberti et al. | |

(Continued)

FOREIGN PATENT DOCUMENTS

| | | |
|---|---|---|
| CN | 101087655 A | 12/2007 |
| CN | 201125246 Y | 10/2008 |

(Continued)

OTHER PUBLICATIONS

Kose, AR et al. Ferrofluid mediated nanocytometry. 2012. Lab on a Chip. 12: 190-196. Published on Nov. 11, 2011. (Year: 2011).*
Non-Final Office Action dated Aug. 8, 2017 for U.S. Appl. No. 14/777,504, 11 pages.
Final Office Action dated Feb. 27, 2018 for U.S. Appl. No. 14/777,504, 10 pages.
Non-Final Office Action dated Apr. 28, 2017 for U.S. Appl. No. 14/777,505, 24 pages.
Final Office Action dated Dec. 20, 2017 for U.S. Appl. No. 14/777,505, 25 pages.
Non-Final Office Action dated Aug. 1, 2017 for U.S. Appl. No. 14/777,512, 18 pages.

(Continued)

*Primary Examiner* — Renee Claytor
*Assistant Examiner* — Susan E. Fernandez
(74) *Attorney, Agent, or Firm* — Cooley LLP (57) ABSTRACT

A device and method for extracting particles contained in a ferrofluid medium are provided. Such methods may comprise suspending particles of different sizes in a ferrofluid medium and containing the ferrofluid medium in a cylindrical reservoir, and applying a first magnetic field to at least a portion of the reservoir. The first magnetic field is configured to indirectly exert a force on at least a portion of the particles of a predetermined size, and direct the portion of particles in a desired direction.

13 Claims, 3 Drawing Sheets

(56) References Cited

U.S. PATENT DOCUMENTS

| | | |
|---|---|---|
| 2003/0235504 A1 | 12/2003 | Lemoff et al. |
| 2004/0018611 A1 | 1/2004 | Ward et al. |
| 2004/0067167 A1 | 4/2004 | Zhang et al. |
| 2004/0096977 A1 | 5/2004 | Rakestraw et al. |
| 2005/0012579 A1 | 1/2005 | Underwood et al. |
| 2005/0233472 A1 | 10/2005 | Kao et al. |
| 2005/0237528 A1 | 10/2005 | Oldham et al. |
| 2005/0244932 A1 | 11/2005 | Harding |
| 2005/0266433 A1 | 12/2005 | Kapur et al. |
| 2005/0280811 A1 | 12/2005 | Sandell |
| 2006/0011305 A1 | 1/2006 | Sandell et al. |
| 2006/0011552 A1 | 1/2006 | Utsunomiya |
| 2006/0013984 A1 | 1/2006 | Sandell et al. |
| 2006/0024690 A1 | 2/2006 | Kao et al. |
| 2006/0024831 A1 | 2/2006 | Kao et al. |
| 2006/0029948 A1 | 2/2006 | Lim et al. |
| 2006/0188399 A1 | 5/2006 | Gu et al. |
| 2006/0166357 A1 | 7/2006 | Takayama et al. |
| 2006/0286549 A1 | 12/2006 | Sohn et al. |
| 2007/0014694 A1 | 1/2007 | Beard et al. |
| 2007/0015289 A1 | 1/2007 | Kao et al. |
| 2007/0125971 A1 | 6/2007 | Lee et al. |
| 2007/0134809 A1 | 6/2007 | Cho et al. |
| 2007/0196820 A1 | 8/2007 | Kapur et al. |
| 2007/0215553 A1 | 9/2007 | Yellen et al. |
| 2007/0224084 A1 | 9/2007 | Holmes et al. |
| 2008/0000892 A1 | 1/2008 | Hirano et al. |
| 2008/0006202 A1 | 1/2008 | Hirano et al. |
| 2008/0035541 A1 | 2/2008 | Franzreb et al. |
| 2008/0038725 A1 | 2/2008 | Luo et al. |
| 2008/0148821 A1 | 6/2008 | Donsky et al. |
| 2008/0210560 A1 | 9/2008 | Barringer |
| 2008/0255006 A1 | 10/2008 | Wang et al. |
| 2008/0302732 A1 | 12/2008 | Soh et al. |
| 2009/0035838 A1 | 2/2009 | Quake et al. |
| 2009/0050569 A1 | 2/2009 | Jung et al. |
| 2009/0078614 A1 | 3/2009 | Varghese et al. |
| 2009/0148933 A1 | 6/2009 | Battrell et al. |
| 2009/0165876 A1 | 7/2009 | Atkin et al. |
| 2009/0175797 A1 | 7/2009 | Warren et al. |
| 2009/0220932 A1 | 9/2009 | Ingber et al. |
| 2009/0227044 A1 | 9/2009 | Dosev et al. |
| 2009/0251136 A1 | 10/2009 | Prins et al. |
| 2009/0325276 A1 | 12/2009 | Battrell et al. |
| 2010/0068824 A1 | 3/2010 | Kimura |
| 2010/0075340 A1 | 3/2010 | Javanmard et al. |
| 2010/0093052 A1 | 4/2010 | Chalmers et al. |
| 2010/0120077 A1 | 5/2010 | Daridon |
| 2011/0003392 A1 | 1/2011 | Stayton et al. |
| 2011/0020459 A1 | 1/2011 | Achrol et al. |
| 2011/0059468 A1 | 3/2011 | Earhart et al. |
| 2011/0065209 A1 | 3/2011 | Heil et al. |
| 2011/0114490 A1 | 5/2011 | Pamula et al. |
| 2011/0124116 A1 | 5/2011 | Wohlstadter et al. |
| 2011/0212440 A1 | 9/2011 | Viovy et al. |
| 2011/0262893 A1 | 10/2011 | Dryga et al. |
| 2011/0312518 A1 | 12/2011 | Davis et al. |
| 2012/0080360 A1 | 4/2012 | Stone et al. |
| 2012/0108470 A1 | 5/2012 | Oh et al. |
| 2012/0178645 A1 | 7/2012 | Foekens et al. |
| 2012/0190589 A1 | 7/2012 | Anderson et al. |
| 2012/0237997 A1 | 9/2012 | Koser |
| 2013/0189794 A1 | 1/2013 | Emeric et al. |
| 2013/0140241 A1 | 6/2013 | Yellen et al. |
| 2013/0313113 A1 | 11/2013 | Koser |
| 2014/0044600 A1 | 2/2014 | McAlister |
| 2014/0214583 A1 | 7/2014 | Assuncao et al. |
| 2014/0283945 A1 | 9/2014 | Jones et al. |
| 2015/0041396 A1 | 2/2015 | Kelly et al. |
| 2016/0016171 A1 | 1/2016 | Goel |
| 2016/0188399 A1 | 6/2016 | Benedict |
| 2016/0263574 A1 | 9/2016 | Smith et al. |
| 2016/0296944 A1 | 10/2016 | Koser |
| 2016/0296945 A1 | 10/2016 | Koser |
| 2016/0299052 A1 | 10/2016 | Koser |
| 2016/0299126 A1 | 10/2016 | Koser |
| 2016/0299132 A1 | 10/2016 | Koser |
| 2017/0122851 A1 | 5/2017 | Thatcher et al. |
| 2017/0259265 A1 | 9/2017 | Diller et al. |
| 2017/0285060 A1 | 10/2017 | Koser |
| 2017/0297028 A1 | 10/2017 | Jones et al. |
| 2018/0029033 A1 | 2/2018 | Koser |
| 2018/0029035 A1 | 2/2018 | Koser |
| 2018/0128671 A1 | 5/2018 | Paur et al. |
| 2018/0128729 A1 | 5/2018 | Koser |
| 2018/0361397 A1 | 12/2018 | Koser |
| 2019/0120822 A1 | 4/2019 | Koser |
| 2019/0339262 A1 | 11/2019 | Koser |
| 2020/0306758 A1 | 10/2020 | Dhlakama |
| 2020/0353466 A1 | 11/2020 | Koser |

FOREIGN PATENT DOCUMENTS

| | | | |
|---|---|---|---|
| WO | WO 1991/001381 A1 | 2/1991 | |
| WO | WO 2006/004558 A1 | 1/2006 | |
| WO | WO 2006/067715 A2 | 6/2006 | |
| WO | WO 2008/042003 A2 | 4/2008 | |
| WO | WO 2010/117458 A1 | 10/2010 | |
| WO | WO 2012/142664 A1 | 10/2010 | |
| WO | WO 2011/071812 A2 | 6/2011 | |
| WO | WO 2011/071912 A1 | 6/2011 | |
| WO | WO 2011/139233 A1 | 11/2011 | |
| WO | WO 2012/057878 A1 | 5/2012 | |
| WO | WO 2013/155525 A1 | 10/2013 | |
| WO | WO 2014/044810 A1 | 9/2014 | |
| WO | WO 2014/144340 A1 | 9/2014 | |
| WO | WO 2014/144782 A2 | 9/2014 | |
| WO | WO 2014/145765 A1 | 9/2014 | |
| WO | WO 2014/065317 A1 | 10/2014 | |
| WO | WO 2017/004595 A1 | 1/2017 | |

OTHER PUBLICATIONS

Final Office Action dated Dec. 22, 2017 for U.S. Appl. No. 14/777,512, 13 pages.

Non-Final Office Action dated Aug. 31, 2018 for U.S. Appl. No. 15/623,134, 12 pages.

Final Office Action dated Apr. 8, 2019 for U.S. Appl. No. 15/623,134, 13 pages.

Non-Final Office Action dated Jan. 20, 2017 for U.S. Appl. No. 14/777,511, 13 pages.

Final Office Action dated Aug. 31, 2017 for U.S. Appl. No. 14/777,511, 12 pages.

Non-Final Office Action dated Jul. 16, 2018 for U.S. Appl. No. 14/777,511, 14 pages.

Final Office Action dated Feb. 21, 2019 for U.S. Appl. No. 14/777,511, 18 pages.

Non-Final Office Action dated Jun. 2, 2017 for U.S. Appl. No. 14/777,507, 10 pages.

Final Office Action dated Nov. 17, 2017 for U.S. Appl. No. 14/777,507, 14 pages.

Non-Final Office Action dated Feb. 12, 2018 for U.S. Appl. No. 14/827,073, 25 pages.

Non-Final Office Action dated Apr. 5, 2019 for U.S. Appl. No. 15/739,466, 8 pages.

Non-Final Office Action dated Jul. 5, 2018 for U.S. Appl. No. 15/740,288, 12 pages.

Non-Final Office Action dated Sep. 14, 2016 for U.S. Appl. No. 13/882,013, 5 pages.

Final Office Action dated Feb. 21, 2017 for U.S. Appl. No. 13/882,013, 6 pages.

Non-Final Office Action dated Sep. 25, 2017 for U.S. Appl. No. 13/882,013, 6 pages.

Non-Final Office Action dated Jul. 31, 2013 for U.S. Appl. No. 13/514,331, 11 pages.

Final Office Action dated Apr. 24, 2014 for U.S. Appl. No. 13/514,331, 16 pages.

Non-Final Office Action dated Apr. 1, 2015 for U.S. Appl. No. 14/591,492, 7 pages.

(56) References Cited

OTHER PUBLICATIONS

Non-Final Office Action dated Jun. 30, 2016 for U.S. Appl. No. 15/163,890, 8 pages.

Final Office Action dated Mar. 13, 2017 for U.S. Appl. No. 15/163,890, 8 pages.

International Search Report and Written Opinion dated Oct. 18, 2011 for International Application No. PCT/US2011/039516, 7 pages.

Examination Report No. 1 dated Nov. 18, 2016 for Australian Application No. 2015268583, 4 pages.

Extended European Search Report dated Dec. 13, 2017 for European Application No. 11836778.8, 9 pages.

International Search Report and Written Opinion dated Feb. 8, 2011 for International Application No. PCT/US2010/059270, 10 pages.

Extended European Search Report dated Dec. 11, 2017 for European Application No. 10836542.0, 10 pages.

International Search Report and Written Opinion dated Aug. 5, 2014 for International Application No. PCT/US2014/028705, 6 pages.

International Search Report and Written Opinion dated Oct. 4, 2014 for International Application No. PCT/US2014/029336, 12 pages.

International Search Report and Written Opinion dated Aug. 11, 2014 for International Application No. PCT/US2014/030584, 7 pages.

International Search Report and Written Opinion dated Aug. 5, 2014 for International Application No. PCT/US2014/029376, 9 pages.

International Search Report and Written Opinion dated Aug. 20, 2014 for International Application No. PCT/US2014/030629, 9 pages.

International Search Report and Written Opinion dated Dec. 23, 2016 for International Application No. PCT/US2016/039394, 8 pages.

International Search Report and Written Opinion dated Sep. 13, 2016 for International Application No. PCT/US2016/040861, 6 pages.

International Search Report and Written Opinion dated Oct. 6, 2017 for International Application No. PCT/US2017/043985, 9 pages.

Applegate et al., "Optical trapping, manipulation, and sorting of cells and colloids in microfluidic systems with diode laser bars," Optical Express 12:4390-4398 (2004).

Ashkin et al., "Optical trapping and manipulation of single cells using infrared laser beams," Nature 330:769-771 (1987).

Ashkin et al., "Optical trapping and manipulation of virsuses and bacteria," Science 235:1517-1520 (1987).

Bautista et al., "Comparative study of ferrofluids based on dextran-coated iron oxide and metal nanoparticles for contrast agents in magnetic resonance imaging," Nanotechnology 15:S154-S159 (2004).

Beyor et al., "Immunomagnetic bead-based cell concentration microdevice for dilute pathogen detection," Biomed Microdevices 10:909-917 (2008).

Blattner et al., "The complete genome sequence of *Escherichia coli* K-12," Science 277:1453-1474 (1997).

Cabrera et al., "Continuous concentration of bacteria in a microfluidic flow cell using electrokinetic techniques," Electrophoresis 22:355-362 (2001).

Castagiuolo et al., "Engineered *E. coli* delivers therapeutic genes to the colonic mucosa," Gene Therapy 12:1070-1078 (2005).

Cheong et al., "Gold nanoparticles for one step DNA extraction and real-time PCR of pathogens in a single chamber," Lab Chip 8:810-813 (2008).

Chiou et al., "Massively parallel manipulation of single cells and microparticles using optical images," Nature 436:370-372 (2005).

Davis et al., "Deterministic hydrodynamics: Taking blood apart," Proc Natl Acad Sci USA 103:14779-14784 (2006).

Dittrich et al., "Lab-on-a-chip: microfluidics in drug discovery," Nat. Rev. Drug Discovery 5:210-218 (2006).

Dufresne et al., "Optical tweezer arrays and optical substrates created with diffractive optics," Rev Sci Instrum 69:1974-1977 (1998).

Dumesny et al., "Synthesis, expression and biological activity of the prohormone for gastrin releasing peptide," Endocrinology 147(1):502-509 (2006).

Fischer et al., Ferro-microfluidic device for pathogen detection, IEEE Int Conf on Nano/Micro Eng and Molecular System China, 907-910 (2008).

Gijs, "Magnetic bead handling on-chip: new opportunities for analytical applications," Microfluidics Nanofluidics 1:22-40 (2004).

Goldman et al., "Slow viscous motion of a sphere parallel to a plane wall—I motion through a quiescent fluid," Chem Eng Sci 22:637-651 (1967).

Green, "The Sigma-Aldrich Handbook of Stains, Dyes & Indicators," Aldrich Chemical Co., Milwaukee, WI, 721-722 (1990).

Han et al., Kynurenine aminotransferase and glutamine transaminase K of *Escherichia coli*: Identity with aspartate aminotransferase, Biochemical Journal 360(3):617-623 (2001).

Horan et al., "Stable cell membrane labeling," Nature 340:167-168 (1989).

Hughes, "Strategies for dielectrophoretic separation in laboratory-on-a-chip systems," Electrophoresis 23:2569-2582 (2002).

Ise, "When, why, and how does like like like?—Electrostatic attraction between similarly charged species," Proc Jpn Acad B Phys Biol Sci 83:192-198 (2007).

Jayashree et al., "Identification and Characterization of Bile Salt Hydrolase Genese from the Genome of Lactobacillus fermentum MTCC 8711," Applied Biochemistry and Biotechnology 174(2):855-866 (2014).

Kamei et al., "Microfluidic Genetic Analysis with an Integrated a-Si:H Detector," Biomed Microdevices 7:147-152 (2005).

Kashevsky, "Nonmagnetic particles in magnetic fluid: Reversal dynamics under rotating field," Phys Fluids 9:1811-1818 (1997).

Kim et al., "Synthesis of ferroflid with magnetic nanoparticles by sonochemical method for MRI contrast agent," J Magn Magn Mater 289:328-330 (2005).

Kim et al., "Cloning and characterization of the bile salt hydrolase genes (bsh) from Bifidobacterium bifidum strains," Applied and Environmental Biology 70(9):5603-5612 (2004).

Kose et al., "Towards Ferro-microfluidics for Effective and Rapid Cellular Manipulation and Sorting," Proceedings of the IEEE Int. Conf. on Nano/Microengineered and Molecular Systems, Jan. 6-9, 2008, pp. 903-906.

Kose et al., "Label-free cellular manipulation and sorting via biocompatible ferrofluids," Proc. Nat'l. Acad. Sci. USA, 106(51):21478-21483 (2009).

Kose et al., "Supporting information to Label-free cellular manipulation and sorting via biocompatible microfluids," Proceedings of the National Academy of Sciences USA; retrieved from the Internet: http://www.pnas.org/content/suppl/2009/12/07/0912138106.DCSupplemental/Appendix.PDF.pdf (2009).

Kremser et al., "Capillary electrophoresis of biological particles: Viruses, bacteria, and eukaryotic cells," Electrophoresis 25:2282-2291 (2004).

Kumar et al., "Molecular cloning, characterization and heterologous expression of bile salt hydrolase (bsh) from Lactobacillus fermentum NCD0394," Molecular Biology Reports 40(8):5057-5066 (2013).

Lee et al., "Microelectromagnets for the control of magnetic nanoparticles," Appl Phys Lett 79:3308-3310 (2001).

Lekka et al., "Elasticity of normal and cancerous human bladder cells studies by scanning force microscopy," Eur Biophys J 28:312-316 (1999).

Liu et al., "Evidence for Localized Cell Heating Induced by Infrared Optical Tweezers," Biophys J 68:2137-2144 (1995).

Maiorov, "Experimental Study of the Permeability of a ferrofluid in an alternating magnetic field," Magneetohydrodynamics 15:135-139 (1979).

Mao et al., "Towards ferrofluidics for μ-TAS and lab on-a-chip applications," Nanotechnology 17:34-47 (2006).

Massart, "Preparation of Aqueous Magnetic Liquids in Alkaline and Acid Media," IEEE Trans Magn 17:1247-1248 (1981).

Menachery et al., Controlling cell destruction using dielectrophoretic forces, NanoBiotechnology 152:145-149 (2005).

Muller et al., "The Potential of Dielectrophoresis for Single-Cell Experiments," IEEE Eng Biol Med Mag 22:51-61 (2003).

(56) References Cited

OTHER PUBLICATIONS

Pethig et al., "Applications of dielectrophoresis in biotechnology," Trends Biotechnol 15:426-432 (1997).
Romasi et al., "Development of Indole-3-Acetic Acid-Producing *Escherichia coli* by Functional Expression of IpdC, AspC, and Iad1," Journal of Microbiology and Biotechnology 23(12):1726-1736 (2013).
Sarsero et al., "A new family of integral membrane proteins involved in transport of aromatic amino acids in *Escherichia-Coli*," Journal of Bacteriology 173(10):3231-3234 (1991).
Sebastian et al., "Formation of multilayer aggregates of mammalian cells by dielectrophoresis," J Micromech Microeng 16:1769-1777 (2006).
Scherer et al., Ferrofluids: Properties and Applications, Brazilian J Phys 45:718-727 (2005).
Steidler et al., "Genetically engineered Probiotics," Baillier's Best Practice and Research. Clinical Gastroenterology 17(5): 861-876 (2003).
Tung et al., "Magnetic properties of ultrafine cobalt ferrite particles," J Appl Phys 93:7486-7488 (2003).
Wang et al., "Expression of rat pro cholecystokinin (CCK) in bacteria and in insect cells infected with recombinant Baculovirus," Peptides 18(9):1295-1299 (1997).
Whelan et al., "A Transgenic Probiotic Secreting a Parasite Immunomodulator for Site-Directed Treatment of Gut Inflammation," Molecular Therapy 22(10):1730-1740 (2014).
Yan et al., "Near-field-magnetic-tweezer manipulation of single DNA molecules," Phys Rev E 70:011905 (2004).
Yellen et al., "Arranging matter by magnetic nanoparticle assemblers," Proc Natl Acad Sci USA 102:8860-8864 (2005).
Zahn et al., "Ferrohydrodynamic pumping in spatially uniform sinusoidally time-varying magnetic fields," J of Magnetism and Magnetic Materials 149:165-173 (1995).
Zhang et al., "A microfluidic system with surface modified piezoelectric sensor for trapping and detection of cancer cells," Biosens Bioelectron 26(2):935-939 (2010).
Zhang et al., "Low temperature and glucose enhanced T7 RNA polymerase-based plasmid stability for increasing expression of glucagon-like peptide-2 in *Escherichia coli*," Protein Expression and Purification 29(1):132-139 (2003).
Final Office Action dated Mar. 16, 2021 for U.S. Appl. No. 16/113,793, 11 pages.
Non-Final Office Action dated Jan. 16, 2020 for U.S. Appl. No. 15/623,134, 10 pages.
Non-Final Office Action dated Jun. 14, 2019 for U.S. Appl. No. 15/982,926, 19 pages.
Final Office Action dated Dec. 12, 2019 for U.S. Appl. No. 15/739,466, 9 pages.
Non-Final Office Action dated Jan. 28, 2021 for U.S. Appl. No. 15/739,466, 9 pages.
Non-Final Office Action dated Jan. 27, 2020 for U.S. Appl. No. 15/708,032, 10 pages.
Non-Final Office Action dated Jul. 12, 2019 for U.S. Appl. No. 15/660,616, 17 pages.
Final Office Action dated Jan. 17, 2020 for U.S. Appl. No. 15/660,616, 14 pages.
Final Office Action dated Mar. 18, 2021 for U.S. Appl. No. 15/660,616, 22 pages.
Non-Final Office Action dated Aug. 22, 2019 for U.S. Appl. No. 15/660,606, 10 pages.
Non-Final Office Action dated Jun. 26, 2019 for U.S. Appl. No. 15/670,264, 11 pages.
First Office Action dated Feb. 20, 2021 for Chinese Application No. 201780060346.2, with English language translation, 12 pages.
International Search Report and Written Opinion dated Feb. 22, 2018 for International Application No. PCT/US2017/065883, 7 pages.
Extended European Search Report dated Jun. 14, 2021 for European Application No. 17934894.1, 6 pages.
Kang et al., "Monitoring of anticancer effect of cisplatin and 5-fluorouracil on HepG2 cells by quartz crystal microbalance and micro CCD camera," Biosensors and Bioelectronics 26:1576-1581 (2010).
Primiceri et al., "Cell chips as new tools for cell biology—results, perspectives and opportunities," Lab Chip 13:3789-3802 (2013).
Asmatulu, R. et al., "A Ferrofluid Guided System for the Rapid Separation of the Non-Magnetic Particles in a Microfluidic Device," Journal of Neuroscience and Nanotechnology, 10:1-5 (2010).

\* cited by examiner

SYSTEMS AND METHODS FOR ACTIVE PARTICLE SEPARATION

RELATED APPLICATIONS

This application is a continuation of U.S. application Ser. No. 14/777,505, filed Sep. 15, 2015, and entitled "Systems and Methods for Active Particle Separation," which is a national stage entry application of and claims priority to International Patent Application No. PCT/US2014/029336, filed Mar. 14, 2014, and entitled "Systems and Methods for Active Particle Separation," which claims benefit under 35 USC 119(e) of U.S. Provisional Patent Application No. 61/794,885, filed Mar. 15, 2013, and entitled, "PCB-Based Magnetic Excitation Approach." The present application incorporates herein by reference the disclosures of each of the above-referenced applications in their entireties.

FIELD OF THE DISCLOSURE

The present disclosure relates to methods and systems for extracting particles from ferrofluids.

BACKGROUND OF THE DISCLOSURE

WO2011/071912 and WO2012/057878 presents systems and methods for separating microparticles or cells contained in a ferrofluid medium using magnetic forces. The magnitude of these forces depend, in part, on the volume of the non-magnetic particles (e.g., moieties) for separation/targeting. Moreover, a larger cell or microparticle displaces a larger ferrofluid volume, and experiences larger forces.

Mechanical exclusion, via well-known filtration is, by its very nature, prone to clogging, and also subsequent increases in pressure drop across the filter as the filter becomes more and more clogged. Such filtration means rely on physically stopping a large enough target particle across a smaller opening on a surface.

SUMMARY OF THE DISCLOSURE

Embodiments of this disclosure are a further application and development of previous series of disclosures, including, for example PCT publication no. WO2011/071912 and WO2012/057878, the noted disclosures of which are all herein incorporated by reference in their entireties.

In some embodiments, methods for extracting particles contained in a ferrofluid medium are provided. Such methods may comprise suspending particles of different sizes in a ferrofluid medium to form a mix and containing the mix in a reservoir (e.g., cylindrical), and applying a first magnetic field to at least a portion of the reservoir. The first magnetic field is configured to indirectly exert a force on at least a portion of the particles of at least one predetermined size and/or shape, and direct the portion of particles in a desired direction.

Such method embodiments may additionally include one or more (or all, as applicable) of the following features (thereby establishing yet other embodiments):

applying includes surrounding at least the portion of the reservoir with the magnetic field;
the particles comprise at least one of biological cells and moieties;
the reservoir includes or is in communication with an extraction opening;
the desired direction is toward the extraction opening;
the desired direction is away from the extraction opening;
the desired direction is toward a central axis the reservoir;
the desired direction is away from a central axis of the reservoir;
the predetermined size comprises smaller particles relative to the remainder of the particles in the ferrofluid medium;
the predetermined size comprises larger particles relative to the remainder of the particles in the ferrofluid medium;
a flow outlet is provided on and/or in communication with the reservoir;
the exerted force is configured such that the portion of particles are carried away in a flow out of the reservoir via the flow outlet;
applying an external force on the reservoir to establish the flow out the flow outlet, where;
the external force is applied via a pressure source, where the pressure source is a pump;
accelerating a flow of the portion of particles via a second magnetic field, the second magnetic field generated by a second magnetic field source arranged on a portion of the reservoir positioned opposite to the extraction opening;
a non-magnetic membrane configured with pore sizes larger than particles within the reservoir to direct particles in a second desired direction;
the second desired direction is toward spaces between the pores of the membrane, wherein the membrane spaces are configured to retain the particles;
the second desired direction is toward the pores of the membrane, such that the particles pass through the membrane;
the non-magnetic membrane comprises a plastic sheet;
the first magnetic field source is configured to reduce the amplitude or substantially eliminate the first magnetic field or the effects thereof;
the amplitude is selected based on the size of the size of the portion of the particles;
a plurality of non-magnetic beads suspended in the ferrofluid, the non-magnetic beads being functionalized with at least one predetermined receptor configured to bind with a target particle;
wherein the at least one predetermined receptor include at least one of a molecule, a cell, an antibody, DNA or fragment thereof, and a ligand;
the magnetic field is configured to direct the target particles toward the space between the pores of the membrane which are configured to retain the target particles; and
detecting means to at least one of track or count the retained target particles.

In some embodiment of the disclosure, systems for extracting particles contained in a biocompatible ferrofluid medium are provided. Such systems may comprise a reservoir (e.g., cylindrical) configured to contain a ferrofluid medium containing particles of different sizes to form a mix, a first magnetic field source configured to indirectly exert a force on the particles to direct at least a portion of the particles of at least one size and/or shape in a desired direction, and an extraction opening arranged on a portion of the reservoir and/or in communication with the reservoir, the extraction opening configured to receive particles of at least one size and/or shape (may be predetermined size and/or shape) from the reservoir as a result of the exerted force.

Such system embodiments, may include one or more (or all, as applicable) of the following additional features (thereby establishing yet other embodiments):

the first magnetic field source is configured to generate a first magnetic field surrounding at least the portion of the reservoir;

the particles comprise at least one of biological cells and moieties;

the desired direction is toward the extraction opening;

the desired direction is away from the extraction opening;

the desired direction is toward a central axis of the reservoir;

the desired direction is away from a central axis of the reservoir;

the predetermined size comprises smaller particles relative to the remainder of the particles in the ferrofluid medium;

the predetermined size comprises larger particles relative to the remainder of the particles in the ferrofluid medium;

a flow outlet provided on and/or in communication with the reservoir;

the exerted force is configured such that the portion of particles are carried away in a flow out of the reservoir via the flow outlet, and wherein the desired direction is away from the extraction opening;

applying a non-magnetic external force on the reservoir to establish the flow out the flow outlet;

the external force is applied via a pressure source, where the pressure source is a pump; and a second magnetic field source arranged on a portion of the reservoir located opposite to the extraction opening, the second magnetic field source configured to generate a second magnetic field on the portion of the particles to accelerate a flow of the portion of particles to the extraction opening;

a non-magnetic membrane configured with pore sizes larger than particles within the reservoir to direct particles in a second desired direction;

the second desired direction is toward spaces between the pores of the membrane, wherein the membrane spaces are configured to retain the particles;

the second desired direction is toward the pores of the membrane, such that the particles pass through the membrane;

the non-magnetic membrane comprises a plastic sheet;

the first magnetic field source is configured to reduce the amplitude or substantially eliminate the first magnetic field or the effects thereof;

the amplitude is selected based on the size of the size of the portion of the particles;

a plurality of non-magnetic beads suspended in the ferrofluid, the non-magnetic beads being functionalized with at least one predetermined receptor configured to bind with a target particle;

the at least one predetermined receptor include at least one of a molecule, a cell, an antibody, DNA or fragment thereof, and a ligand;

the magnetic field is configured to direct the target particles toward the space between the pores of the membrane which are configured to retain the target particles; and detecting mean to at least one of track or count the retained target particles (such detecting means being well known in the art).

The above-noted embodiments, as well as other embodiments, will become even more evident with reference to the following detailed description and associated drawing, a brief description of which is provided below.

DETAILED DESCRIPTION OF SOME OF THE EMBODIMENTS

Figure 1:
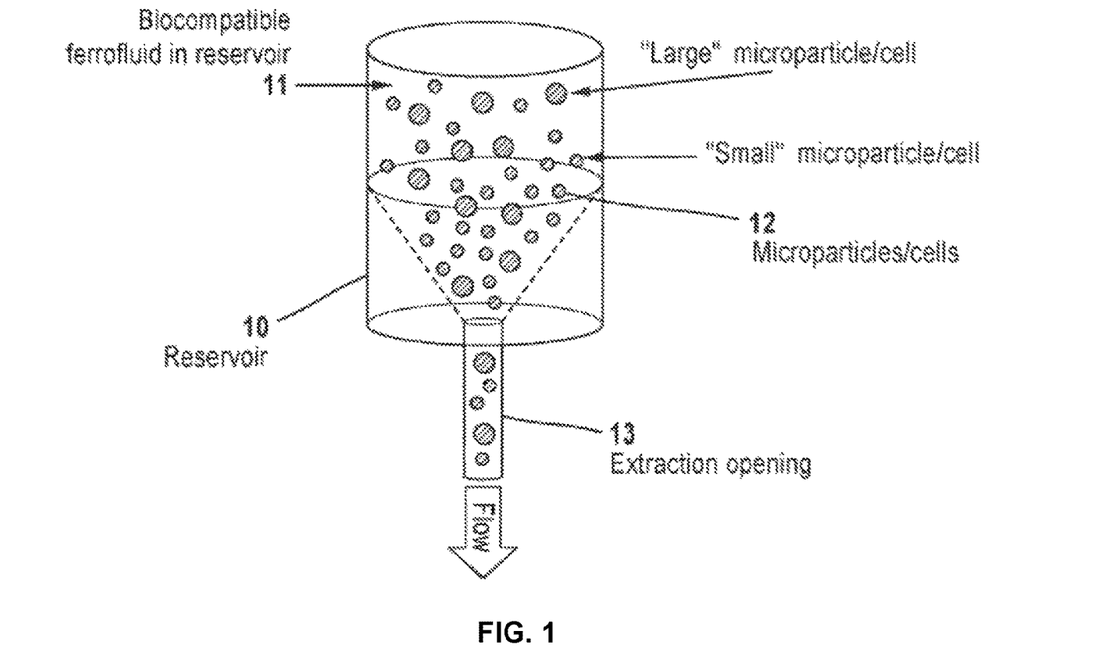
FIG. 1 is an illustration depicting structures of a reservoir and associated structures containing a ferrofluid and a mixture of microparticles, according to some embodiments.

As shown in FIG. 1, a reservoir 10 containing a ferrofluid 11 (which in some embodiments is biocompatible) and a mixture of microparticles/cells 12 having different sizes (in some embodiments). In FIG. 1, no external forces are applied to the fluid, reservoir and/or particles, and ignoring buoyancy issues, a random mixture of particles may flow through an extraction opening 13 of the reservoir.

Figure 2:
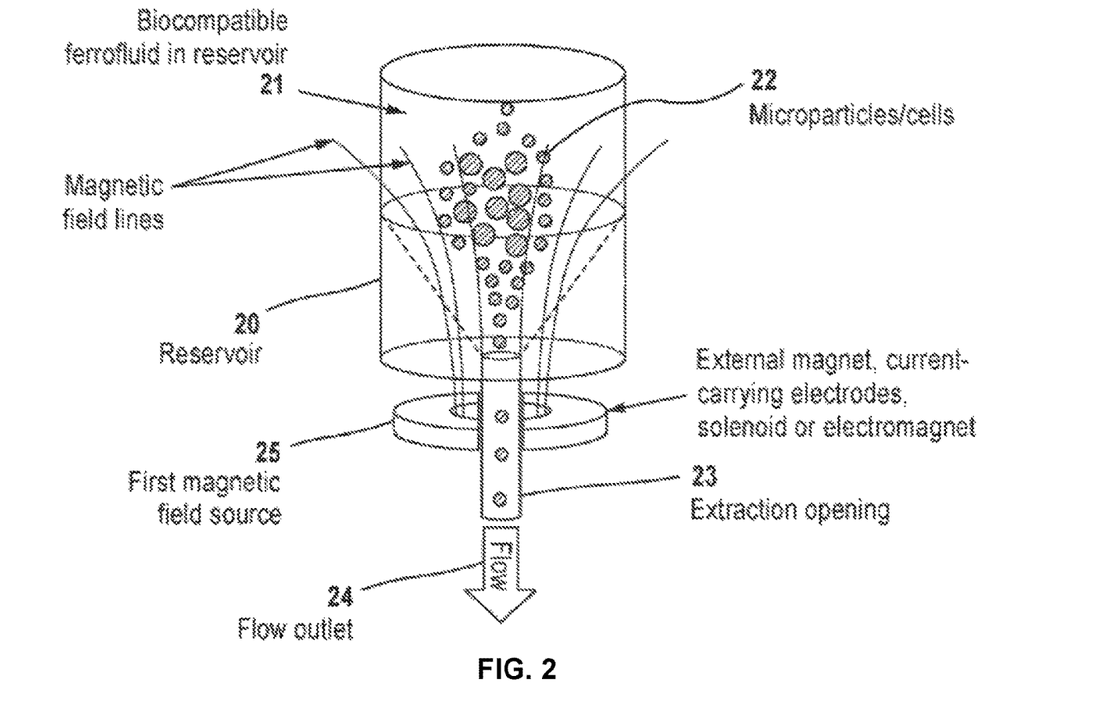
FIG. 2 is an illustration depicting structures of a reservoir and associated structures containing a ferrofluid and a mixture of microparticles, including a magnetic source for applying a magnetic field to the reservoir, according to some embodiments.

FIG. 2 illustrates some embodiments, where a reservoir 20 containing a ferrofluid 21 with a mixture of microparticles 22 of different sizes, and includes at least one magnetic source 25 for applying a magnetic field to the ferrofluid 21, which may be arranged either internal or external to the reservoir 20. The particles 22 include biological cells and moieties. The magnetic field may be configured to exert one or more forces on the ferrofluid 21 and may be generated via, for example, one or more: external magnets, current-carrying electrodes, solenoid, and electromagnets. In one embodiment, the magnetic field may surround at least a portion of the reservoir 20. The reservoir 10 includes or is in communication with an extraction opening 23. The force(s) exerted by the magnetic fields on the ferrofluid 21 cause the particles 22, in some embodiments, to be directed in a desired direction. Such a desired direction may be toward the extraction opening 23, away from the extraction opening 23, toward a central axis of the reservoir 20, and away from a central axis of the reservoir 20, according to some embodiments. The particles 22 include, in one embodiment, smaller particles relative to the remainder of the particles 22 in the ferrofluid 21 and larger particles relative the remainder of the particles 22 in the ferrofluid 21. The larger particles feel much larger repulsive forces, and can hence be dynamically levitated above the outlet, whereas the smaller particles will be dragged out with flow. In one embodiment, a flow outlet 24 is provided on and/or in communication with the reservoir. The exerted force may be configured to carry away a portion of particles 22 in a flow out of the reservoir 20 via the flow outlet 24. Such a flow out of the reservoir 20 may be generated via an external force, for example, a pressure source or a pump.

It is possible to create a magnetic field pattern around a sample reservoir or vial carrying microparticles or cells suspended within a biocompatible ferrofluid in order to push those moieties either toward or away from an extraction hole. This approach and the device that achieves this manipulation could be used in the context of either speeding or delaying the delivery of the target moieties from the volume of the reservoir into the fluidic cartridge downstream. The magnitude of this magnetic force would depend in part on the intensity of the magnetic field sources, as well as their relative geometry with respect to that of the reservoir. The magnetic force also depends on the ferrofluid susceptibility and the volume of the microparticles/cells. Hence, the pushing force, in conjunction with the flow rate out of the reservoir/vial into the extraction hole, could be engineered such that moieties larger than a selectable threshold volume could be continuously and dynamically repelled away the vial's outlet under steady state conditions. In this fashion, moieties larger than the selectable threshold volume could be excluded from the fluidic network downstream.

What is described here is an "active pre-filter" that works on dynamic magnetic exclusion principles in steady-state flow and magnetic excitation conditions. Most other size-based filtration methods rely on mechanical obstacles (such as pore sizes of a given diameter in filter paper or micro fabricated devices) and work on static mechanical exclusion principles.

The active pre-filter described here avoids the shortcomings of mechanical filters by achieving size-based separation and exclusion within the 3D volume of the vial/reservoir, instead of the 2D surface of a mechanic filter (FIGS. 1 and 2). Those microparticles or cells that are larger than the selectable threshold are continuously suspended and mixed in the biocompatible ferrofluid, hence preventing large scales of clustering and possible clogging issues.

Even if the filtered moieties tend to cluster within the ferrofluid, their increased overall hydrodynamic diameter will result in substantially larger repulsion forces on them. With flow drag roughly proportional to the hydrodynamic diameter ($\sim d$) and magnetic forces proportional to the hydrodynamic volume ($\sim d^3$), the larger cluster will be pushed further away from the outlet. Hence, this active pre-filter features a negative feedback mechanism that naturally prevents potential clogging issues (FIG. 2).

Figure 3:
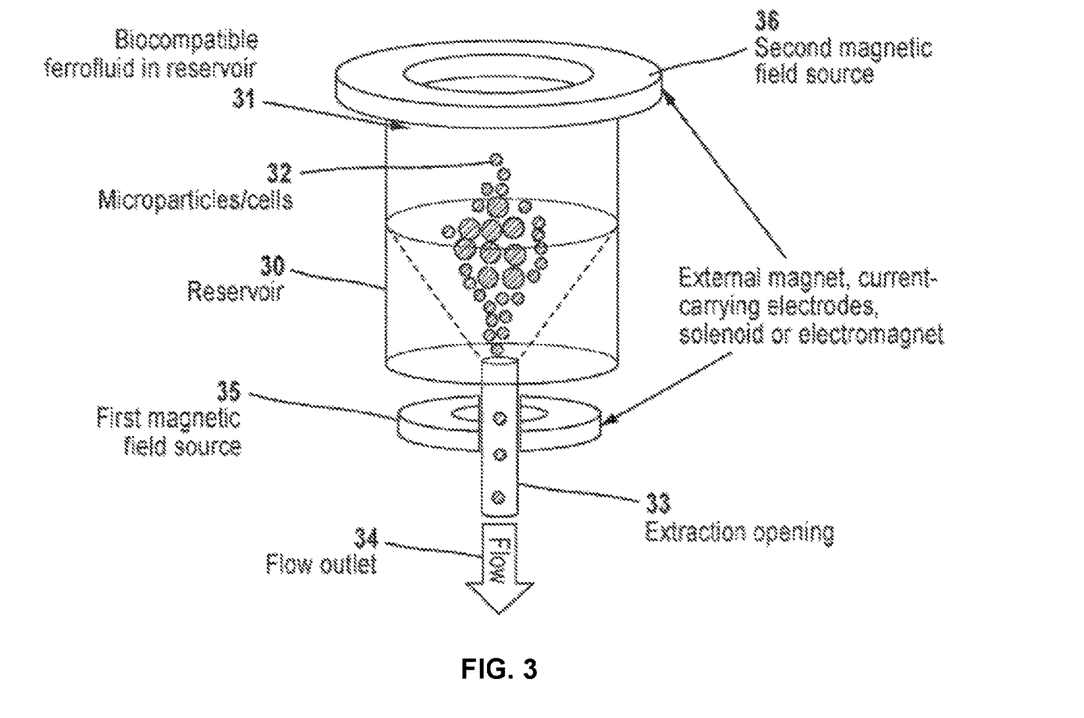
FIG. 3 is an illustration depicting structures of a reservoir and associated structures containing a ferrofluid and a mixture of microparticles, including two magnetic sources for applying one or more magnetic fields to the reservoir, according to some embodiments.

FIG. 3 illustrate some embodiments, where a reservoir 30 containing a ferrofluid 31 and a mixture of microparticles 32 with different sizes. A second magnetic field source 36 maybe place opposite the extraction opening 33 to accelerate the transport of microparticles 32 towards it. In this fashion, the effect of any other forces (such as buoyancy) on the delivery efficiency of target particles/cells 32 to the fluidic network downstream may be minimized. The larger particles would also cluster and levitate closer to the outlet, the relative intensity of the two field sources may be tuned to prevent any cluster from clogging the outlet. Moreover, clusters may be broken by periodic intensity modulations in at least one field sources.

It may be necessary to intentionally and periodically stir up the contents of the vial so as to break up clusters of large microparticles or cells. This will ensure that anything smaller than the selection threshold is not impeded by or somehow stuck within the clusters. This effect might be easily achieved by modulating the intensity of the externally applied magnetic field and allowing the flow to break the dynamic clusters apart (FIG. 3).

In the simplest realization of the active pre-filter, a vial/reservoir with cylindrical symmetry sits on top of a tunable source of magnetic fields, preferably encompassing similar symmetry in its geometry. The magnetic field and its gradient are designed to push the target moieties suspended in a biocompatible ferrofluid up and towards the center of the vial, into the region of strongest flow (away from the vial's interior surfaces). The biocompatible ferrofluid is pulled into an extraction hole at the center bottom of the vial via externally imposed flow conditions (e.g., a pump or pressure device). The intensity of the magnetic field and its gradient are engineered so as to push moieties larger than a selectable size up and away from the vial's outlet at the bottom faster than the maximum flow rate near the vicinity of the outlet. In certain instances, a recirculation region within toroidal symmetry is formed around the outlet, capturing and circulating the filtered moieties. In other geometries, the filtered moieties hover dynamically a certain distance over the outlet. In such cases, as the filtration progresses, the filtered moieties are intentionally allowed to cluster and pushed further up.

Figure 4:
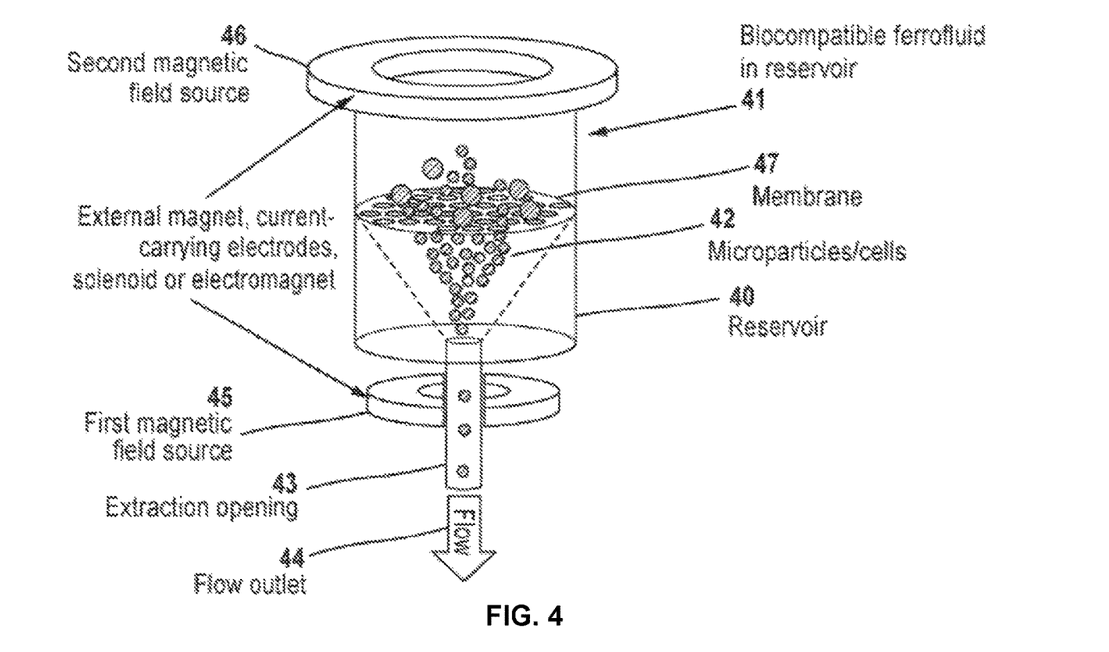
FIG. 4 is an illustration depicting structures of a membrane with pore sizes larger than the individual particles/cells placed within a reservoir containing a ferrofluid medium.

FIG. 4 illustrates some embodiments, where a reservoir 40 containing a ferrofluid 41 and a mixture of microparticles 42 with different sizes. A first magnetic field source 45 placed proximate to the extraction opening 43 and a second magnetic field source 46 placed opposite of the first magnetic field source 45 to accelerate the transport of microparticles 42 toward the extraction opening 43.

In some embodiments, a non-magnetic membrane 47 configured with pore sizes larger than microparticles 42 within the reservoir 40 containing the ferrofluid mix 41 of ferrofluid and target particles is provided. Such membranes function to capture target particles using magnetic fields. For example, in the absence of externally applied magnetic fields, micro/target particles/cells may flow through the membrane's pores. However, upon applying a magnetic fields, the non-magnetic membrane 47 may be configured to direct debris, particulate contaminants and microparticles/cells 42, larger than a size threshold value (for example), away from the pores of the membrane and into the space between the pores. Particles 42 smaller than the threshold, in some embodiments, tend to follow flow streamlines and pass through the non-magnetic membrane 47.

The non-magnetic membrane, in one embodiment, is made out of a plastic sheet. In addition, in some embodiments, the pores may be configured as any size (on a scale relative to the teachings herein, e.g., pore sizes of 1-200 μm, 5-50 μm, 10-100 μm, 20-30 μm), and any shape, including, for example, round, circular, polygonal, rectangular/slit, square, and/or elliptical. In some embodiments, the shape of the pores is configured to aid in the intended functionality of capturing particles using magnetic forces and not by pore size (i.e., pore size relative to target particle size), such that the overall pore size, in some embodiments, is larger than the target particle size.

A plurality of pores, according to some embodiments, may be arranged in predetermined patterns (i.e., not random), and may be configured in such a manner to aid in the capture functionality of the membrane feature. Thus, groups of pores on the same or different size, shape, etc., may be arranged in repeated groups or matrix. Such pores may be manufactured into a sheet of material, by, for example, laser etching.

Figure 5:
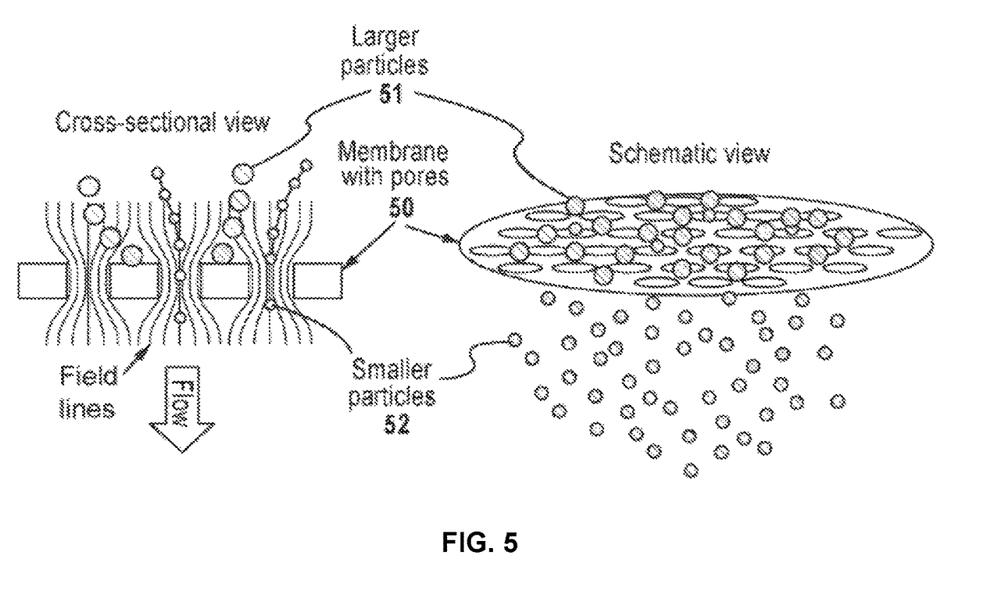
FIG. 5 is an illustration depicting the cross-sectional and schematic view of a membrane with pores within a ferrofluid medium.

FIG. 5 illustrates some embodiments, magnetic field lines prefer to stay within the magnetic medium of the ferrofluid.

If the porous membrane 50 is made out of a non-magnetic material (such as a thin sheet of plastic), field lines traversing its thickness get concentrated within the pores. This effect results in stronger field amplitudes within the pores, compared to just outside them—thereby creating a magnetic field gradient that pushes particles up and away from the pores. Since the magnetic force on particles is proportional to the volume of ferrofluid that they displace, larger particles 51 tend to accumulate over the membrane 50 in the space between the spores, while small particles 52 follow flow streamlines and pass through the membrane 50.

In some embodiments, the porous membrane may be made from a thin foil of a magnetic material configured with a magnetic susceptibility which is greater than that of the ferrofluid at the magnetic excitation frequencies used (for example). For instance, such magnetic membranes may be machined out of a thin foil of nickel via, for example, lithographic etching or laser machining. Accordingly, upon the application of a magnetic field (e.g., external magnetic field), the magnetic field lines traversing the thickness of the magnetic membrane tend to remain within the membrane material. This effect, according to some embodiments, may result in weaker field amplitudes within the pores compared to just outside them, which thereby creates a magnetic field gradient that can push the non-magnetic particles towards the pores. In some embodiments, if magnetic beads are added to the sample mixture, they may be attracted towards the surface of the magnetic membrane between the pores. In this same fashion, functionalized magnetic beads may be used to rapidly pull down, isolate and purify target moieties in biocompatible ferrofluids.

The porous membrane is not absolutely necessary for the active filter to function, but by creating strong and localized field gradients, it allows for a much more robust and easily tunable size-based separation.

When the fields are lowered in magnitude or turned off completely, the retained particles/cells can be selectively released back into the flow stream. For instance, in an assay that is conducted with a mixture of whole blood and blood-compatible ferrofluid, platelets, red blood cells and white blood cells may be sequentially retained and selectively entered into the assay channels by reducing the magnetic field amplitude appropriately for each cell size. Hence, with the use of the active pre-filter, labor- and time-intensive cell separation techniques (such as centrifugation) may be rendered redundant, resulting in much quicker and simpler assay protocols. The field magnitudes may be sequentially controlled and timed by a microprocessor as part of an automated assay.

In yet another embodiment, multiple membranes may be stacked serially along the fluidic pathway, and may be exposed to the same magnetic field sources (for example). Each membrane may be positioned parallel to others in the stack and, in some embodiments, at least partially orthogonal to the flow direction. In some embodiments, a minimum spacing between each membrane is chosen to correspond to at least their thickness, so that field line density has space to return to normal between each membrane (i.e., in some embodiments, this is provided to avoid one membrane from interfering with the filtering ability of its neighbor). In some embodiments, using stacked, non-magnetic membranes with progressively smaller pore sizes, a complex mixture with various cell/particle sizes (such as whole blood) may be fractionated very rapidly based on size.

In some embodiments, the porous membrane may be used to rapidly immobilize and hold down functionalized beads over its surface. These beads would carry at least one kind of receptor molecule, antibody, DNA fragment and other ligand on their outer surface. As the beads are held on the membrane with magnetic fields, a mixture of target and non-target moieties may be flown through the active filter and rapidly captured on the "carpet" of beads sitting over the porous membrane. The target moieties may be small molecules, proteins, complementary DNA fragments, viruses, bacteria or even larger cells. Once the target moieties have been captured on the beads and isolated from the initial mixture, they could be either tagged and quantified directly on the porous membrane, or be released into the assay chamber for further processing and quantification. With this approach, what is normally a lengthy and labor-intensive sample preparation, incubation and isolation process can be reduced to an automatic and rapid step within a simple instrument.

In some embodiments, actual bacteria and cells are held on the porous membrane surface with magnetic fields, and can be exposed to molecular tags, candidate drug molecules, antibodies or other proteins, with the express purpose of dramatically accelerating the incubation processes associated with binding ligands to cellular surface biomarkers.

The porous membrane may also be functionalized with ligands that capture the pathogens or cells held on its surface. This approach is especially useful if it is desired to have target pathogens or cells remain on the membrane surface while other moieties present in the initial sample mixture are washed away when the magnetic fields are turned down (such as in sample purification or immune-sorbent assays). As such, the active filter not only solves the mass transport limitations associated with incubation steps in molecular or cellular assays, it also avoids the labor-intensive washing steps that typically follow binding/capture reactions.

Any and all references to publications or other documents, including but not limited to, patents, patent applications, articles, webpages, books, etc., presented in the present application, are herein incorporated by reference in their entirety.

Example embodiments of the devices, systems and methods have been described herein. As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and devices which may further include any and all elements from any other disclosed methods, systems, and devices, including any and all elements corresponding to target particle separation, focusing/concentration. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Correspondingly, some embodiments of the present disclosure may be patentably distinct from one and/or another reference by specifically lacking one or more elements/features. In other words, claims to certain embodiments may contain negative limitation to specifically exclude one or more elements/features resulting in embodiments which are patentably distinct from the prior art which include such features/elements.

What is claimed is:

1. A method for extracting particles contained in a ferrofluid medium comprising:
   suspending a plurality of particles of different sizes in a ferrofluid medium to form a mixture;
   containing the mixture within a reservoir including a first end having an extraction opening,
   providing a membrane configured with a plurality of pores, each pore of the plurality of pores including a pore size;
   and
   applying at least one magnetic field to the reservoir via a first magnetic field source located proximate to the first end of the reservoir,
   wherein the at least one magnetic field is configured to exert an indirect force on the plurality of particles resulting in:
      a first portion of the plurality of particles having a first size greater than a predetermined threshold size being directed away from the pores of the membrane,
      a second portion of the plurality of particles having a second size smaller than the predetermined threshold size being directed through the pores of the membrane, and
      the first size of each particle of the first portion of the plurality of particles, and
      the second size of each particle of the second portion of the plurality of particles, are less than the pore size.

2. The method of claim 1, wherein applying the at least one magnetic field includes surrounding at least the portion of the reservoir with the magnetic field.

3. The method of claim 1, wherein the plurality of particles further comprise at least one of biological cells and moieties.

4. The method of claim 1, further comprising applying an external force on the reservoir to establish flow.

5. The method of claim 4, wherein the external force is applied via a pressure source.

6. The method of claim 5, wherein the pressure source is a pump.

7. The method of claim 1, further comprising accelerating a flow of the second portion of the plurality of particles through the pores of the membrane via a second magnetic field generated by a second magnetic field source arranged adjacent a second end of the reservoir opposite the first end.

8. The method of claim 1, wherein the first portion of the plurality of particles are directed away from the pores of the membrane to spaces between the pores of the membrane.

9. The method of claim 1, wherein the membrane comprises a plastic sheet.

10. The method of claim 1, wherein the mixture further comprises a plurality of non-magnetic beads having at least one receptor to bind with a target particle of the plurality of sample particles.

11. The method of claim 10, wherein the at least one receptor includes at least one of a molecule, a cell, an antibody, DNA or fragment thereof, and a ligand.

12. A method for extracting particles contained in a ferrofluid medium comprising:
   suspending a plurality of particles of different sizes in a ferrofluid medium to form a mixture;
   containing the mixture within a reservoir including a first end having an extraction opening, providing a membrane configured with a plurality of pores; and
   applying at least one magnetic field to the reservoir via a first magnetic field source located proximate to the first end of the reservoir,
   wherein the at least one magnetic field is configured to exert an indirect force on the plurality of particles resulting in:
   a first portion of the plurality of particles having a first size greater than a predetermined threshold size being directed away from the pores of the membrane, and
   a second portion of the plurality of particles having a second size smaller than the predetermined threshold size being directed through the pores of the membrane,
   and wherein the membrane is configured to reduce amplitude of or substantially eliminate the at least one magnetic field.

13. The method of claim 12, wherein the amplitude of the at least one magnetic field is selected based on the threshold size.

* * * * *